(12) United States Patent
Thoms

(10) Patent No.: US 6,982,411 B2
(45) Date of Patent: Jan. 3, 2006

(54) LIGHT DETECTOR UNIT FOR A DEVICE FOR READING FLEXIBLE STORAGE FOILS

(75) Inventor: Michael Thoms, Bietigheim-Bissingen (DE)

(73) Assignee: Durr Dental GmbH & Co. KG, (DE)

( * ) Notice: Subject to any disclaimer, the term of this patent is extended or adjusted under 35 U.S.C. 154(b) by 120 days.

(21) Appl. No.: 10/444,313

(22) Filed: May 23, 2003

(65) Prior Publication Data

US 2003/0202636 A1 Oct. 30, 2003

Related U.S. Application Data

(60) Division of application No. 10/087,182, filed on Mar. 1, 2002, now Pat. No. 6,599,014, which is a continuation of application No. PCT/EP00/08604, filed on Sep. 2, 2000.

(30) Foreign Application Priority Data

Sep. 3, 1999 (DE) ................................ 199 42 211

(51) Int. Cl.
*H01J 40/14* (2006.01)
(52) U.S. Cl. ..................................... 250/239; 250/235
(58) Field of Classification Search ................ 250/239, 250/234, 235, 226, 584, 585; 360/93, 132, 360/137; 369/44.14, 44.16
See application file for complete search history.

(56) References Cited

U.S. PATENT DOCUMENTS

| | | | | |
|---|---|---|---|---|
| 4,816,923 A | * | 3/1989 | Saotome | ...................... 358/489 |
| 4,939,715 A | * | 7/1990 | Vogelgesang et al. | ......... 360/93 |
| 6,599,014 B2 | * | 7/2003 | Thoms | ....................... 378/184 |

* cited by examiner

*Primary Examiner*—Que T. Le
(74) *Attorney, Agent, or Firm*—Factor & Lake

(57) ABSTRACT

A device for reading flexible storage foils. The devices includes a foil support, a reading light source which provides a reading light beam which has a wave length suitable to excite metastable storage centers of the storage foil. Drive mechanisms are employed to provide relative movement between the reading light beam and the storage foil. A light detector is responsive to fluorescence light of the storage foil generated by the reading light beam.

24 Claims, 13 Drawing Sheets

LIGHT DETECTOR UNIT FOR A DEVICE FOR READING FLEXIBLE STORAGE FOILS

The present application is a divisional of U.S. application Ser. No. 10/087,182, filed on Mar. 1, 2002, which is now U.S. Pat. No. 6,599,014, which was a continuation of PCT Patent Application No. PCT/EP00/08604 filed Sep. 2, 2000, claiming priority from German Patent Application DE 19942211.7 filed Sep. 3, 1999.

BACKGROUND OF THE INVENTION

1. Field of the Invention

The invention relates to a device for reading flexible storage foils.

2. Background Art

Recently, flexible storage foils are being used instead of X-ray films. When ionizing radiation or X-rays impinge on such foils, metastable storage centers will be produced, which are lattice defects or color centers (or generally trap centers), which have trapped a charge carrier (electron or hole) produced by the ionizing radiation. Such storage centers are stable over long times. If the storage centers are illuminated with a very narrow laser beam of corresponding wave length, the storage centers will be moved into a higher excited state, from which the charge carriers can recombine under emission of light called photo-stimulated luminescence (PSL). The latter process is also shortly referred to as recombination of storage centers.

At such points of the storage foil, whereon a larger amount of X-rays has impinged, one obtains by reading this point using a reading light beam, a higher amount of light quanta than at such points, which have received only a few X-rays. If the storage foil is scanned in two dimensions, the output signals of a light detector receiving the PSL corresponds to the optical density of a conventional X-film.

In known reading devices, two dimensional scanning of the storage foil is obtained by arranging the storage foil on the outer surface of a drum, by rotating the drum and by moving a reading unit along a generating line of the drum. The reading unit includes a laser source and a light detector.

Such drum type scanners, which are also known for scanning images, are disadvantageous in that they have larger moving masses and in that the scanning velocity which can be achieved is only small due to this fact so that the scanning process takes a long time. It is thus an object of the present invention provide a reading device, wherein the moving masses are smaller and which allows high scanning velocities and short scanning times.

In a reading device in accordance with the present invention the storage foil support has the form of a part cylinder or of a cylinder, and a light deflecting element is arranged on the axis of this cylinder's surface. This deflecting element produces a fine rotating reading light beam, which scans the interior surface of the storage foil. This light deflecting element requires only very small dimensions and is of small mass, only. Due to this construction, the reading device in accordance with the present invention can work well with higher speed or rpm.

These and other objects of the present invention will become apparent in light of the present specification, claims and drawings.

SUMMARY OF THE INVENTION

If in accordance with the present invention, a pentaprism is used as the deflecting element for the reading light beam, one obtains a particularly precise deflection. The reflection of the reading light beam is exactly at 90° with respect to the axial direction of irradiation and into a radial measuring direction not withstanding whether the prism is exactly aligned or not. Also play of a bearing journaling a prism carrying shaft has no influence on the deflection of the reading light beam. Thus motors of simple construction showing some play of the shaft can be used for rotating the light deflecting element without impairing the precision of the deflection of the light.

The improvement of the present invention allows the use of the light deflecting element also for focusing the reading light beam onto the interior surface of the storage foil. In one preferred embodiment, there is a reading light source which already per se provides a reading light beam of very small cross section and small divergence. This makes it possible to construct the light deflecting element as a very small component.

A further improvement of the invention is advantageous in view of a compact structure of the reading device and makes it possible to arrange the reading light source also at a distance from the axis of the cylindrical surface.

In a preferred embodiment of the invention, both mirrors of the reading device, which deflect the light, which is provided by the laser on an axis being parallel to the axis of the support surface, exactly onto the axis of the support surface, are in fixed relative position since the two deflecting mirrors are part of a single rigid optical element. This is advantageous in view of reducing the adjusting steps.

A further improvement is advantageous in that only a single deflecting mirror is necessary to provide an incoming laser beam on the axis of the foil support.

In another preferred embodiment, the reading light beam of a semiconductor laser diode has a circular cross section which results in pixels of the scanned image which have equal dimension in the two scanning directions.

The present invention is advantageous in view of utilizing as much of the fluorescence light as possible. A further advantage resides in the fact that the efficiency in detecting fluorescence light, which is emitted along the scanning circle by the storage foil, is constant. Thus no subsequent corrections of the detected fluorescence signals are necessary.

The light detector of the present invention may have a smaller radius so that the costs for the detector are smaller. In spite of this advantage, the light generated at a larger radius can still be used due to the annular mirror reflecting this light onto an opposing mirror which will then reflect the light into the light detector.

The improvement of the present invention is also useful in view of using as much of the fluorescence light as possible, which light is emitted by the storage foil after illumination with laser light.

In a preferred embodiment of the invention, the light deflecting element can be driven directly without an intermediate direction changing gear by a motor that is arranged behind or in the mirror opposing the light detector.

In this respect, the improvement of the invention is advantageous in that such light is guided to the light detector, which impinges onto the mirror under large angles (grazing impingement). Thus the detection efficiency for fluorescence light is increased. Since the measured intensity of the fluorescence light is proportional to the intensity of the laser light as well as proportional to the detection efficiency, one can reduce the intensity of the laser light and still obtain the same sensitivity of demeasuring system. This is advantageous in that low cost laser light sources can be used.

In accordance with the present invention, the mirror opposing the light detector can also serve as an absorbing layer for reading light. Thus, undesired reflections of the laser light can be avoided, which could result in storage centers lying in regions of the foil, which are not yet to be scanned, being already caused to fluoresce. This would result in poorer resolution of the image. Also the contrast of the storage foil would be noticeably impaired.

The geometry of the mirror can have a large radial extension without having large axial extension and without requiring thin wall sections in the radial outward portion thereof. Also, transport means provided to feed the storage foils across a reading gap defined by the foil support, can be arranged close to the axial end of the mirror which is advantageous in view of precisely advancing the storage foil in axial direction at the location of the reading gap.

In such a preferred embodiment, reflected light will not travel in circumferential direction for a longer time but will be diffusely reflected to the light detector.

If the mirror is a cast component, the optical surfaces of the mirror can be already provided in the casting process. These surfaces need none or very little final treatment.

The present invention is likewise advantageous in still further reducing the amount of reading light which reaches the light detector.

In another preferred embodiment of the invention, as much of the fluorescence light as possible is detected by increasing the overall detecting surface. Thus a maximum amount of fluorescence is made available for the production of electric signals.

It is contemplated that solutions for driving the light deflecting element in a way that the light deflecting element and the drive motor associated thereto require only little space.

In a preferred embodiment of the invention, PSL originating from the scanning circle (intersection of the plane of rotation of the reading light beam and the light sensitive interior surface of storage foil bent to cylindrical or part cylindrical geometry) is used for generating an electric signal in both half spaces, i.e. on both sides of the plane of rotation of the reading light beam.

In the present invention, reading light is kept way from the detector. In addition, undesired reflections of reading light are avoided, which could read the storage foil at other points distant from the actually scanned point and which could thus result in faulty reading of the storage foil.

The storage foil to be read out is arranged on the outer surface of the foil support member. In spite of this fact, the reading light beam has complete access to the interior surface of the storage foil throughout 360°.

In a preferred embodiment of the invention, very simple arrangement of the storage foil on the foil support and the force generated in the elastically bendable storage foil warranting a snug contact of the storage foil on the support surface of the foil support is allowed. This is advantageous in view of reducing imperfect definition or sharpness of the image which may result from unprecise radial positioning of the storage foil outside of the focusing circle of the reading light.

Furthermore, better protection of the light detector against ambient light is provided for.

If the light blocking brush element is formed, movement of the storage foil through the light barrier formed by the brush element is possible under small friction and thus small wear.

In another preferred embodiment, advantageous solutions for keeping the storage foil in safe surface contact with the supporting surface of the foil carrier without mechanically affecting the front side of the storage foil which is prone to formation of scratches is contemplated.

The present invention likewise provides a solution as to providing the axial movement of the storage foil with respect to that transverse plane wherein the reading light beam rotates in a simple manner.

The improvement of the present invention is useful in that the danger of tilting of the storage foil under the influence of the transport means acting in axial direction is eliminated.

The improvement of the invention is advantageous in view of a good and reliable frictional contact between the transport means and the storage foil.

In a preferred embodiment, a large area of contact between the transport means and the storage foil results, such that uncontrolled slip between the transport means and the storage foil is avoided.

A reading device of the present invention is useful in that no reading light can escape. Furthermore no ambient light can reach the light detector without being attenuated.

The improvement of the present invention warrants that reading light, which possibly transverses the storage foil (in the case of a storage foil having no absorbing back layer) or which otherwise reaches the shielding member or a foil guiding member, will be absorbed and will not be reflected back to the storage foil, which might again result in faulty reading as has been pointed out above. The indicated construction of the shielding member and/or the foil guiding member allows to use also such storage foils which do not include a back layer absorbing the reading light.

The present device allows feeding of small storage foils, e.g. storage foils replacing conventional dental intraoral X-ray films directly to the working run of the axial drive means without exerting special diligence.

In the present device, positioning of the small storage foils is made at a point close to the input end of the axial drive means so no misalignment may occur on the way between the positioning means and the input end of the second drive means.

The present device allows tactile positioning of the small storage foils.

Furthermore, there is a smooth transition between the positioning means and the support surface of the foil support.

In a preferred embodiment of the invention, a plurality of small storage foils can be read out simultaneously.

Measuring the angular position of the read out light beam using a mechanical or optomechanical position encoder would mean a very costly encoder considering the desired resolution of the image. Also this encoder would have to measure the angular position at a high measuring rate. It is contemplated that a reliable and precise signal being representative for the angular position of the reading light beam is obtained using simple mechanical and electronic components.

In a device of the present invention, at least regions of the image(s) are rapidly stored in a memory. This allows preprocessing and rejection of signals which do not correspond to pixels of the desired image reading the device already before forwarding the image signals to a computer for further processing.

In a device of the present invention, the actual dark current of the light detector is measured continuously. In accordance with the measured dark current, a dark current threshold value can be set which is used in setting the image signals associated to image points receiving no light to zero.

In a device of the present invention, the flux of data to be communicated to an external processor is reduced. This allows use of a relatively slow interface which is commercially available. Averaging of successive image signals is also advantageous in view of improving the signal to noise ratio.

In a preferred embodiment of the invention, the number of image signals combined into an averaged signal can be varied. Normally high resolution of the image is required in connection with dental intraoral images which are of small size, while a somewhat reduced resolution is acceptable in connection with dental panoramic images. So the total amount of information to be handled by the electronics associated to the device is about the same in connection with panoramic images and intraoral images.

In such a device the extent of averaging is established automatically in accordance with the size of the foil to be scanned.

Recognition of the foil size is particularly simple in accordance with the present invention. If a small storage foil is recognized in the foil positioning means of the foil support the device is set into the high resolution mode.

A further improvement of the invention is also advantageous in view of reducing the flux of data communicated to an external processor.

In a device in accordance with the present invention, the image signals associated to a plurality of small size intraoral storage foils can be rapidly stored in an image signal memory of the device itself. Transfer of the image data to an external data processing unit can then be made at a smaller rate using a commercial interface.

In a preferred embodiment of the present invention, only those of the output signals provided by the light detector are used, which correspond to image points of the storage foils, while those portions of the output signals which correspond to positions of the reading point which are outside of the storage foils arranged on the foil support are discarded. Recognition of the edges of the storage foils can be simply achieved by detecting a succession of a given number of non zero image signals by the data reduction circuit.

In accordance with storage foils of different size or different nature it is desirable to vary the gain of the light detector. This can be achieved using a device in accordance with the present invention.

In a device of the present invention, the gain of the light detector is automatically adjusted responsive to the size of the storage foil arranged on the foil support, the size being an indicator for the sensitivity of the storage foil and for the dose conditions during exposure.

In such a device the detector gain can be wholly or at least partially adjusted manually. This allows some basic adjustment of the detector gain in accordance with local scanning conditions and in accordance with the type of storage foils and optical densities a particular dentist or doctor prefers to use.

The present invention is advantageous in view of the little space used by the device. Also there is some gravity feeding of the storage foils in regions, where there are no positive axial drive means. It is also advantageous in view of ease of removal of read out storage foils. Furthermore, the read storage foils are particularly easy to grasp.

BRIEF DESCRIPTION OF THE DRAWINGS

The invention will now be described with reference to the drawings wherein.

DETAILED DESCRIPTION OF THE DRAWINGS

Figure 1:
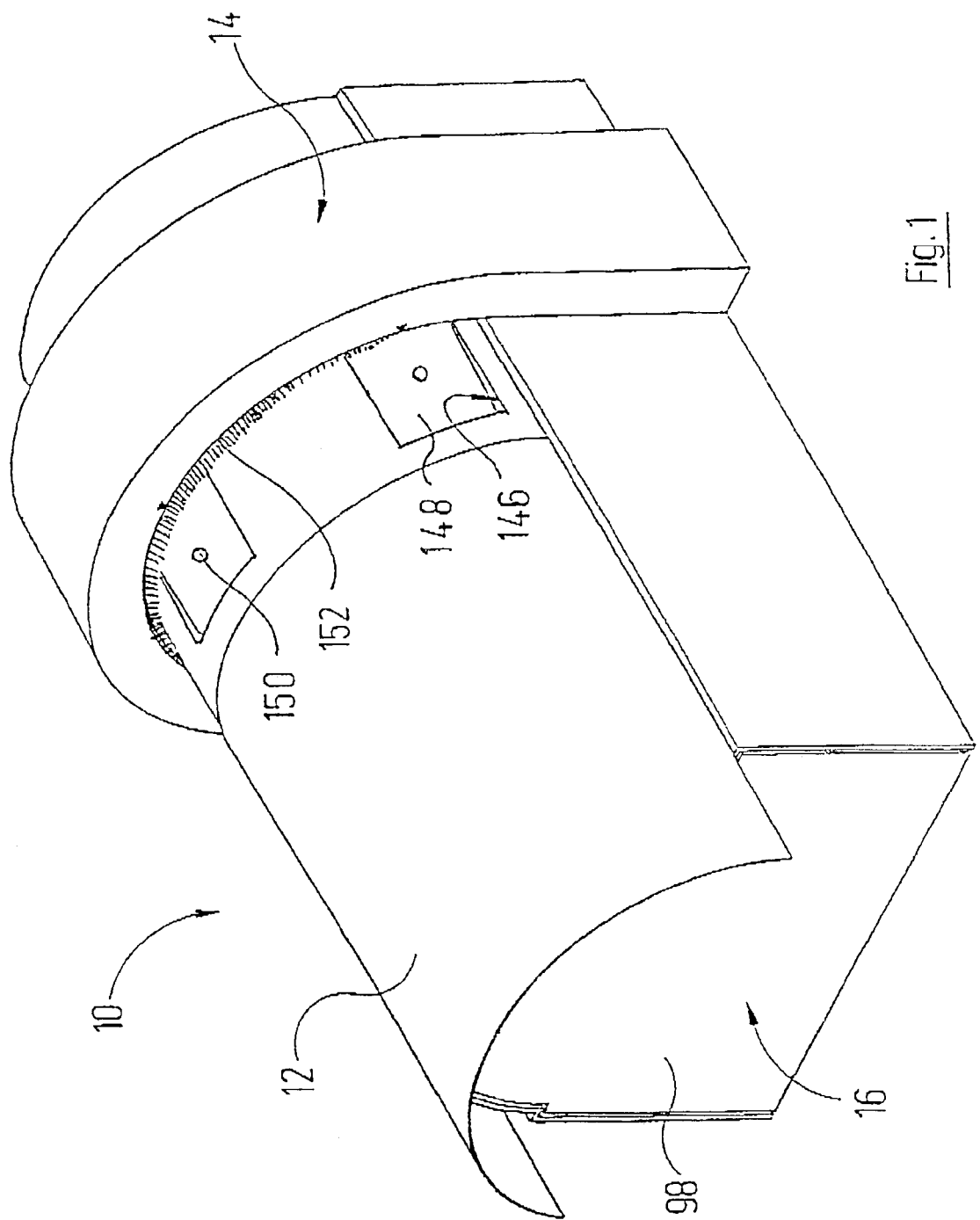
FIG. 1 is a perspective view of a scanner for reading storage foil seen from the loading side.

FIG. 1 shows a scanner generally shown at 10 for reading out an optical storage foil 12. The storage foil 12 has the form of a rectangular sheet and is made from a flexible plastics substrate, a large number of phosphor particles being evenly distributed and embedded into the substrate. Alternatively the substrate may be coated homogeneously with a large number of phosphor particles. The distance of the phosphor particles is very small to warrant high resolution of the storage foils. Typical mean distances between the phosphor particles are in the range of a few $\mu$m.

The phosphor particles are made from a storage phosphor material, e.g. an alkali halide or alanine earth halide salt, which is appropriately doped (e.g. with heavy metal ions) such that upon exposure to ionizing radiation metastable storage centers are formed therein. The dope of the salt is chosen such that the storage centers have metastable states which can be populated by X-ray light, particularly such X-ray light which is used in medical diagnosis. Such metastable states are stable for periods ranging from some 10 minutes up to an hour. If laser light of appropriate wave length (e.g. red light) is irradiated into the metastable states of the storage centers, the metastable storage centers will be transferred into higher excited states from which the charge carriers can recombine generating fluorescence light (PSL). The PSL typically is blue light.

If the optical excitation of the excited color centers is made using a reading light beam of very small cross section (10 $\mu$m to 50 $\mu$m), reading of the excited color centers, the density of which corresponds to the intensity of the X-ray light, is also only local. If the fluorescence light is transmitted to a light detector, e.g. a photomulitplier, one obtains an electric signal corresponding to the X-ray intensity in the considered measuring or reading point. By moving the reading beam across the storage foil in two mutually perpendicular coordinate directions one can obtain a X-ray image which has been converted into electric signals.

The scanner shown in FIG. 1 has a scanning and transport unit generally shown at 14 as well as well a detector unit generally shown at 16. The detector unit 16 is positively engaged and received in the scanning and transport unit 14.

Referring to FIGS. 2 to 6 the scanning and transport unit 14 will now be described in detail. The scanning and transport unit 14 has a main housing body 18, the transverse cross section of which generally corresponds to the cross section of a gutter. Two vertical walls 22, 24 are formed integral with a bottom wall 20 extending parallel the longitudinal axis of the latter. The vertical walls 22, 24 include an angled shoulder 26 extending towards the median plane of the housing. The free ends of the shoulder 26 carry a semicylindrical support wall 28.

In the claims and the description of the present application the axis of the support wall 28 will also be shortly referred to as "the axis" of the reading device.

Figure 2:
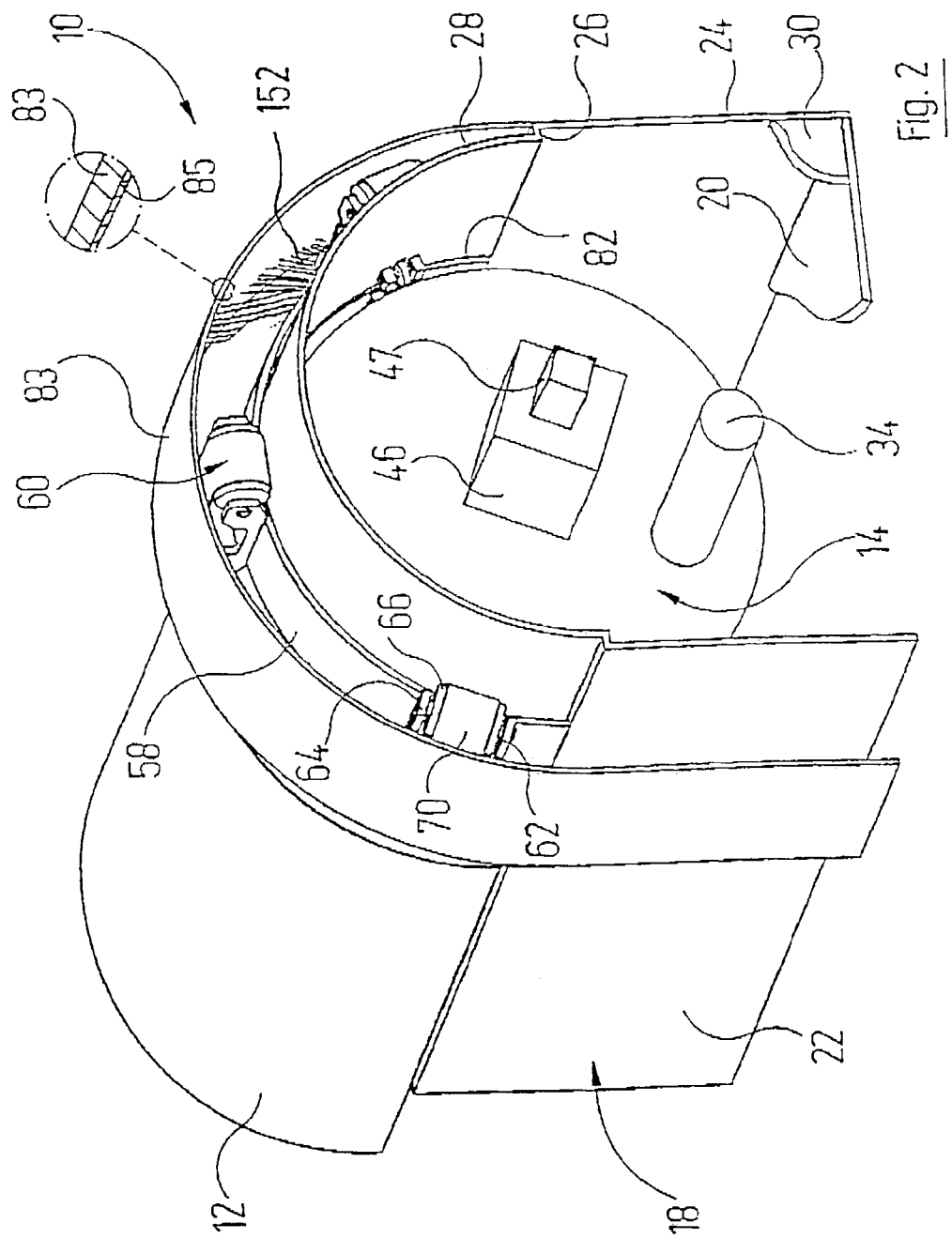
FIG. 2 is a perspective view of the scanner of FIG. 1 seen from the foil discharge side, an end wall of the housing being partially broken away.
Figure 3:
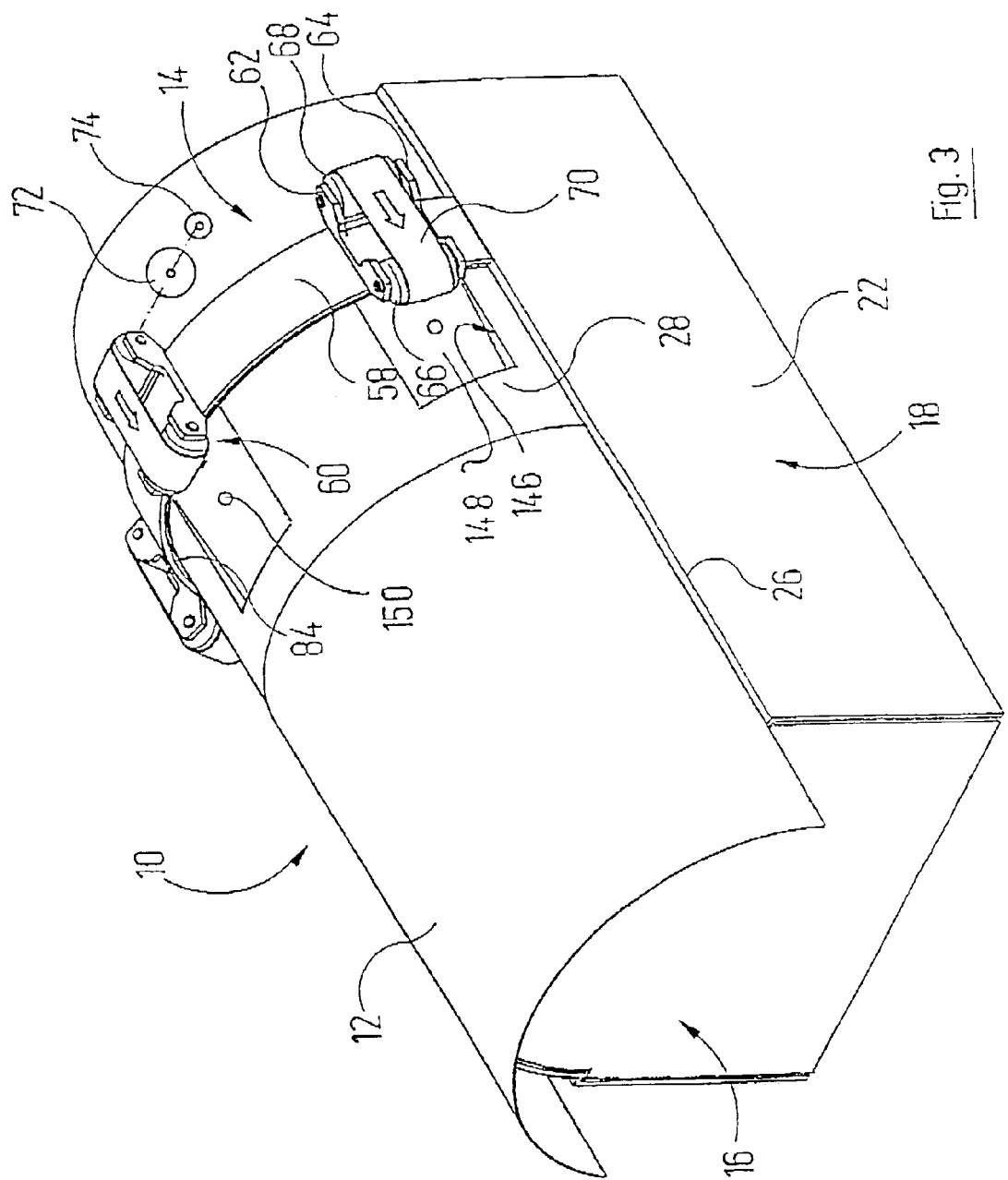
FIG. 3 is a perspective view of a scanning and transport unit of the scanner shown in FIGS. 1 and 2 as seen from the loading side.

The end of the main housing body 18 being the front end in FIG. 2 is closed by a flush end wall 30.

In a region being closer to the exit end of the main housing body 18 the main housing body 18 carries an intermediate wall 32 having the form of a circular disk. The intermediate wall 32 in a lower portion thereof carries a rod shaped laser 34 providing a focused reading light beam 36 of very small diameter. The rod shaped laser 34 extends parallel to the axis of the support wall 28, the laser axis thus being spaced from the axis of the support wall 28. Typically the diameter of the reading light beam 36 in the focus can be between 10 $\mu$m and 50 $\mu$m which corresponds to a resolution of the X-ray image, which is carried by the storage foil 12 in the form of correspondingly distributed metastable excited color centers, being from 10 to 50 line pairs/mm.

Figure 4:
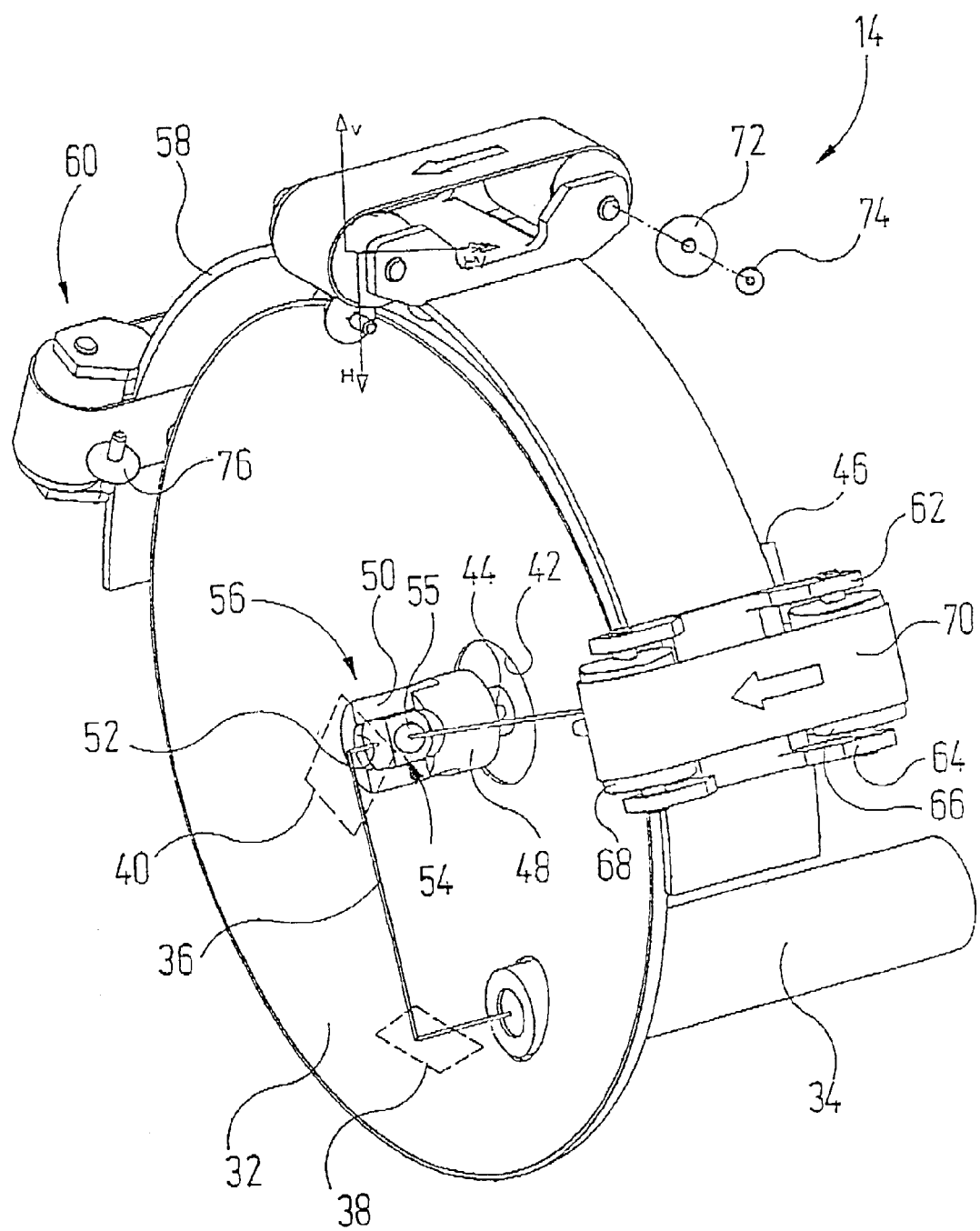
FIG. 4 is a perspective view of the main parts of the scanning and transport unit of FIG. 3 shown in enlarged scale.
Figure 5:
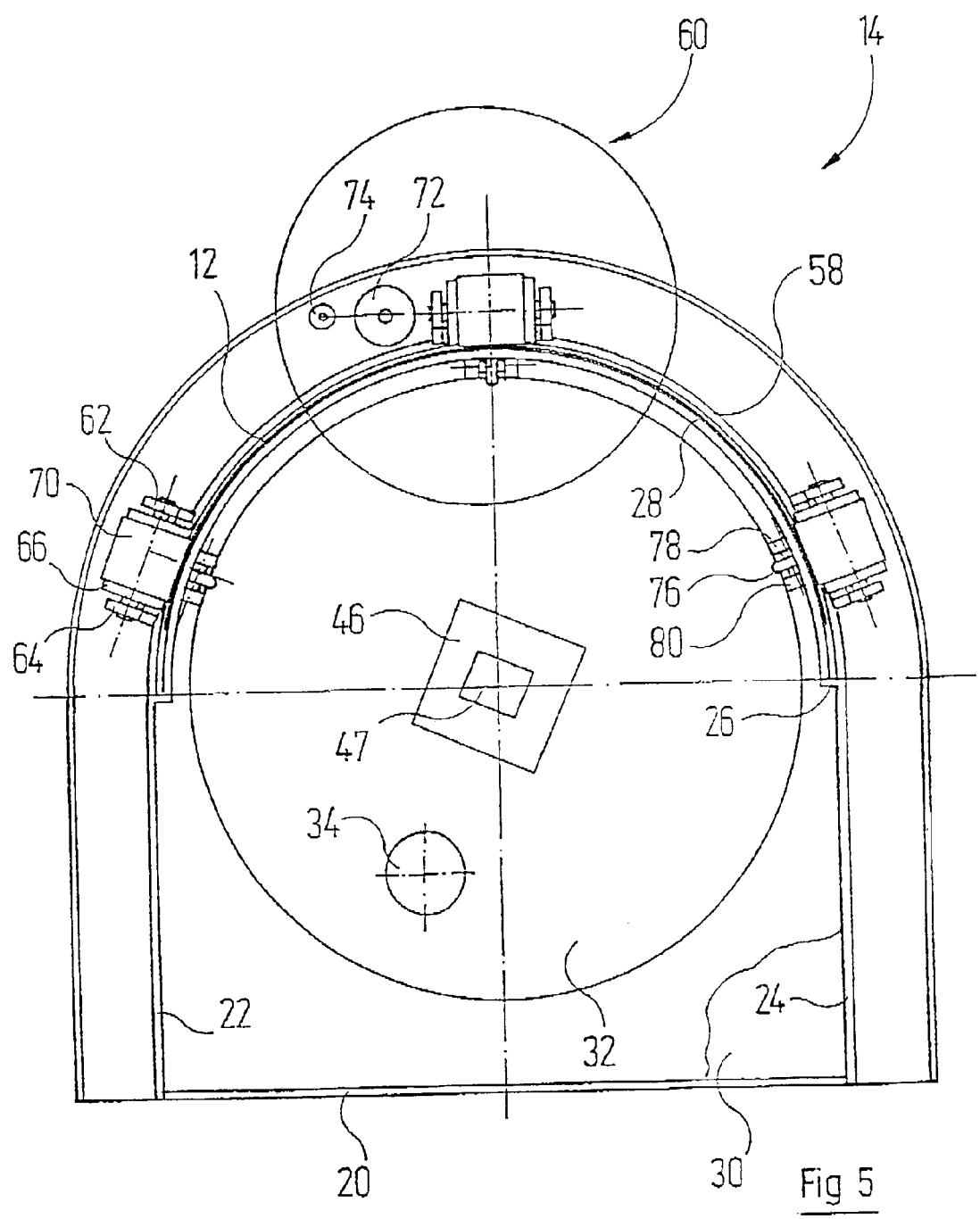
FIG. 5 is a transverse section of the scanning and transport unit of FIG. 3, the section being taken in the plane, in which the reading light beam rotates.
Figure 6:
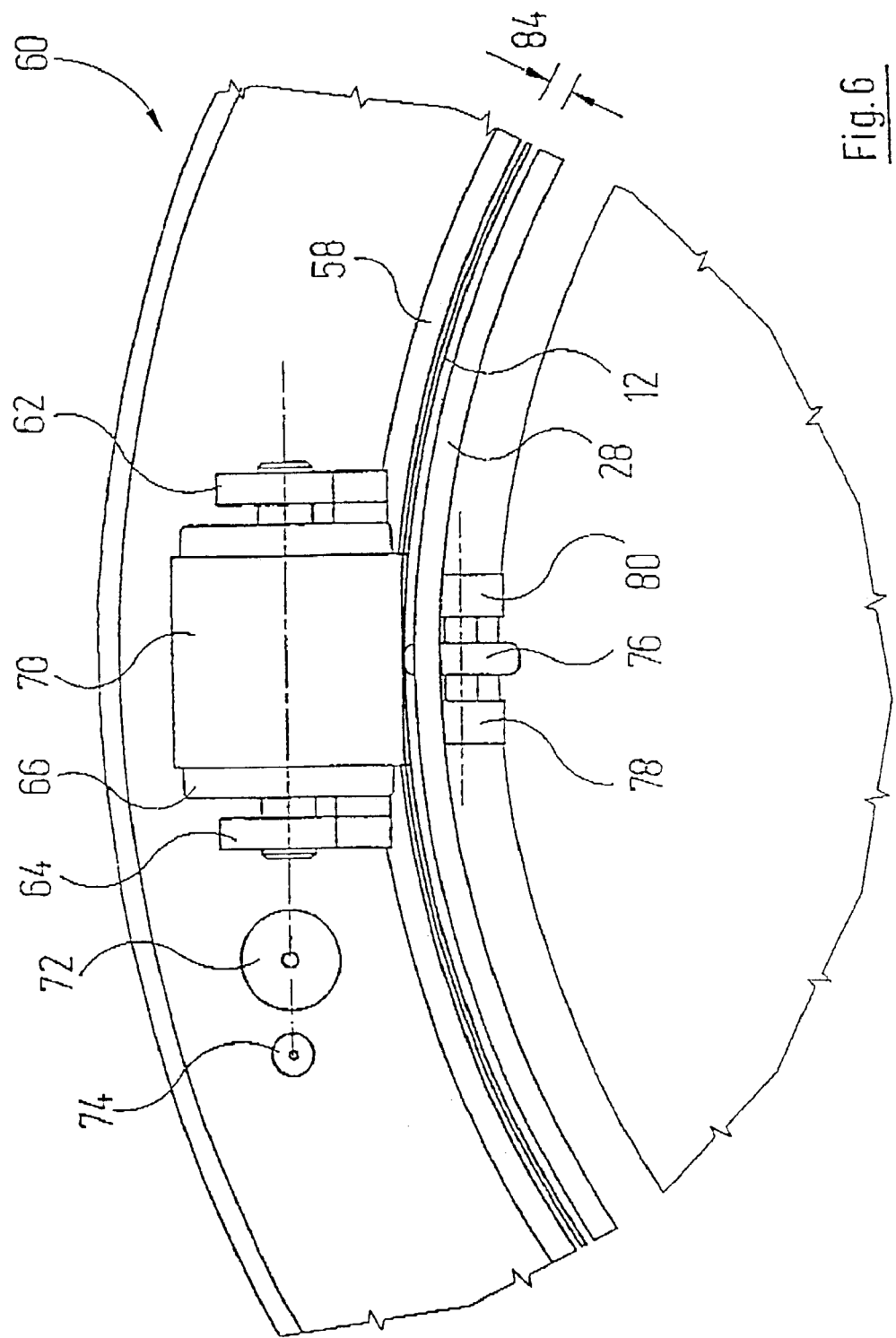
FIG. 6 is a still enlarged representation of the foil transport unit.

As may be seen from FIG. 4, the reading light beam 36 is deflected onto the axis of the support wall 28 using two 45° deflecting mirrors 38, 40 which are carried by the main housing body 18 in a way which is not shown in detail in the drawings.

The intermediate wall 32 has a central shaft opening 42 receiving a motor shaft 44 of an electric drive motor 46 carried by the rear side of the intermediate wall 32. The motor shaft 44 carries a cylindrical prism carrying member 48, a quarter of which has been milled off as shown at 50.

A receptacle 52 formed in the prism carrying member 48 receives a pentaprism 54. The latter deflects the read out light beam 36 in radial direction. For focusing the read out light beam 36 to the interior surface of the storage foil 12 a collecting lens 56 is arranged on the exit surface of the pentaprism 54, e.g. by glueing the lens thereon to or by forming this lens integral therewith.

The components 36 to 54 described above co-operate to form a deflecting unit 56, which makes the reading light beam 36 rotate in a transverse plane also referred to herein as the beam plane or plane of rotation of the beam.

A semicylindrical narrow mounting member 58 carries three transport units generally shown at 60. These transport units each have two spaced opposing journaling walls 62, 64 each journaling one end of two rollers 66, 68, respectively. A transport belt 70 runs on the rollers 66, 68. The transport belt 70 is made from a material cooperating with the material of the storage foil 12 under high friction. The various transport units 60 each comprise a drive motor 72 carrying a position encoder 74. The various transport units 60 are electrically synchronized by means of a control unit not shown in FIGS. 1 to 7.

A pressure roller 76 is associated to the radial inward working runs of the transport belts 70, respectively. The pressure rollers 76 are mounted at the interior surface of the support wall 28 for free rotation by means of journaling lugs 78, 80.

In the plane of rotation of the read out light beam 38 the support wall 28 is formed with a slot 82 extending in circumferential direction (see FIG. 2). Thus the read out light beam 36 reaches the light sensitive side of a storage foil 12 which contains the phosphor particles. The storage foil 12 is arranged on the support wall 28 such that its sensitive side faces the axis of the support wall 28.

A shield wall 83 surrounds the transport units 60 being coaxial to the mounting member 58. The inward surfaces of the shield wall 83 are provided with a layer 85 absorbing the reading light. Thus it is possible, if desired, to also use storage foils which have no backing absorbing the reading light.

Scanning of the storage foil 12 using the scanning and transport unit 14 as described above is obtained as follows:

The storage foil 12 is arranged on the support wall 28 such that its storage layer faces in downward direction. The storage foil 12 is moved into the gap 84 defined between the mounting member 58 and the support wall 28 in a correspondingly curved state. In this gap the storage foil 12 is engaged by the working run of the transport belts 70, the pressure roller 76 warranting a predetermined frictional contact between the convex rear side of the storage foil 12 and the transports belts 70. The transport belts 70 are driven in continuous manner and the drive motor 46 is energized. Consequently the storage foil 12 is scanned along a helical line in a continuous manner. The helical line has a width corresponding to the diameter of the read out light beam 36, a radius corresponding to the radius of the support wall 28 and a pitch corresponding to the speed of the transport belts and the rpm of the deflecting unit. The actual point at which the read out light 36 hits the storage foil 12 (reading point) can be recognized from the output signals of a position encoder 47 associated to the motor 46 and of the position encoder 74.

The detector unit 16 serves for measuring the fluorescence light obtained at the respective actual reading points. As may be seen in more detail from FIG. 7, the detector unit 16 has a detector housing 86 including a bottom wall 88. Vertical walls 90, 92 are formed integral with the lateral edges of the bottom wall 88. The upper ends of the vertical walls 90, 92 carry inwardly extending shoulders 94 and a cylindrical support wall 96 as well as an end wall 98 closing the left hand end of the detector housing 86 as shown in the drawings.

One recognizes that the outer contour of the detector housing 86 is chosen so as to allow positive engagement of the detector housing 86 in the left hand portion of the main housing body 18.

A large diameter photomulitplier 100 is arranged in the support wall 96 such that its entrance window 102 is adjacent to the slot 82. A color filter 104 is arranged across the entrance window 102, which filter is transparent for fluorescence light but blocks the reading light.

If the output signal of the photomulitplier 100 is recorded together with the output signals of the position encoders 47 and 74 one obtains an electric image of the X-ray image previously formed in the storage foil 12 in the form of exited metastable color centers of the phosphor particles. This image can then be further processed electrically in view of changing the scale of reproduction, emphasizing details, improving the signal/noise ratio and so on. The X-ray image can also be put into an archive in its original and/or digitally processed form requiring only little space.

Figure 8:
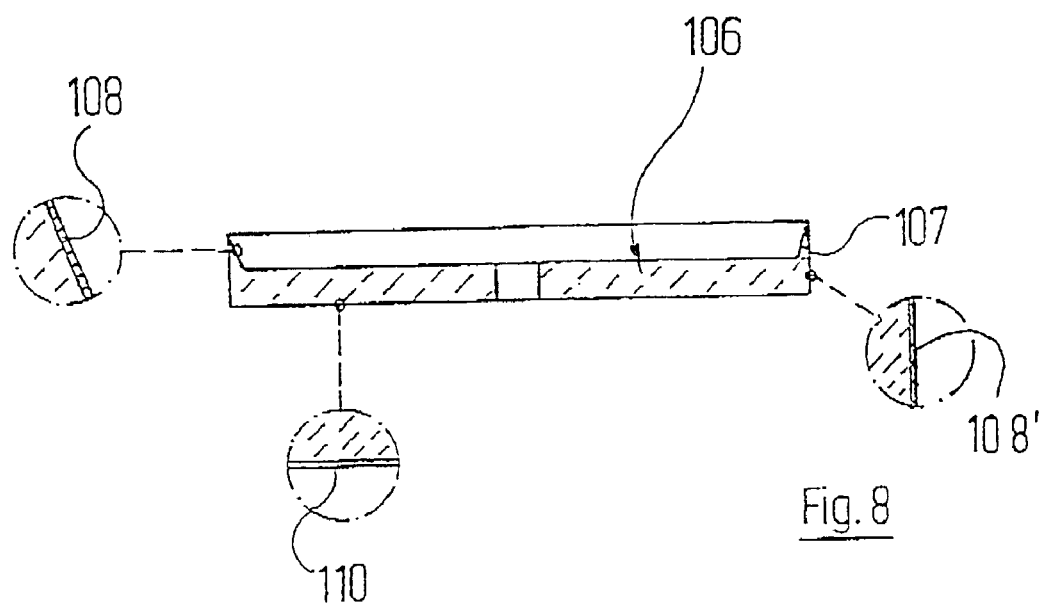
FIG. 8 is a section through an optical component of the scanning and transport unit, which at the same time forms a filter, a mirror as well as a shielding element.

Once the storage foil 12 has been read out, it is entirely irradiated with erasing light to erase eventual remnant storage centers. Thereafter the storage foil can be used for taking a further X-ray image. In order to be able to profit from the fluorescence light directed from the reading points into the right hand half space for measurement purposes, the intermediate wall 32 can be formed as a mirror. One way of doing so will now be described referring to FIG. 8.

A color filter 106 is made from a material which is transparent for fluorescence light and absorbs reading light. A frusto-conical peripheral wall 107 of the color filter carries a reflecting layer 108. A further reflecting layer 110 is arranged on the back side of the color filter 106.

Alternatively the circumferential reflecting layer may be arranged on the exterior circumferential surface of the color filter 106 as shown at 108'. Thus this layer can be easily deposited together with the layer 110 and the reflected light will be filtered.

Due to provision of the color filter 106 it is impossible that reading light after reflection will again impinge onto the light sensitive surface of the storage foil 12, which might result in faulty reading out of the storage foil as has been pointed out above. On the other hand fluorescence light, that originating from the actual reading point is directed into the right hand half space as seen in the drawings, will be reflected into the entrance window 102 of the photomultiplier 100.

Figure 9:
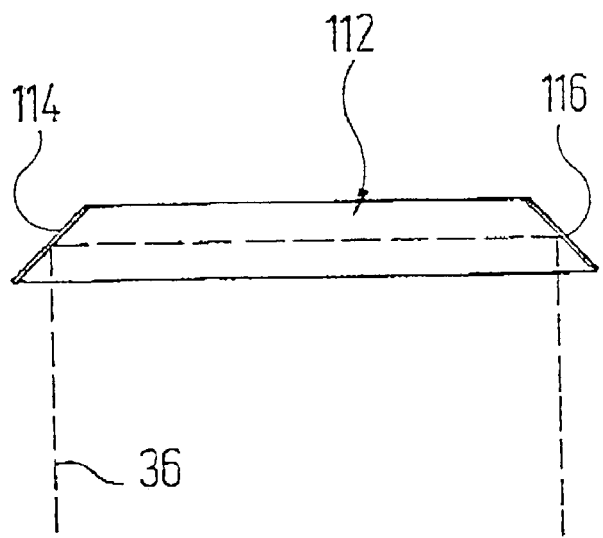
FIG. 9 is a lateral view of an optical wave guide carrying two light deflecting layers.

FIG. 9 shows a one piece optical wave guide 112, which is of rod shaped geometry. The two ends thereof are provided with 45° inclined end faces and on each of these two inclined end faces deflecting layers 114, 116 are provided. The one piece optical wave guide 112 thus can replace the two deflecting mirrors 38, 40 which facilitates mounting and adjusting of the scanning and transport unit.

In the modified embodiment in accordance with FIG. 10 components, the functions of which correspond to the function of components already described in connection with FIGS. 1 to 10 have been given the same reference numerals. These components need not be described in detail below.

Figure 10:
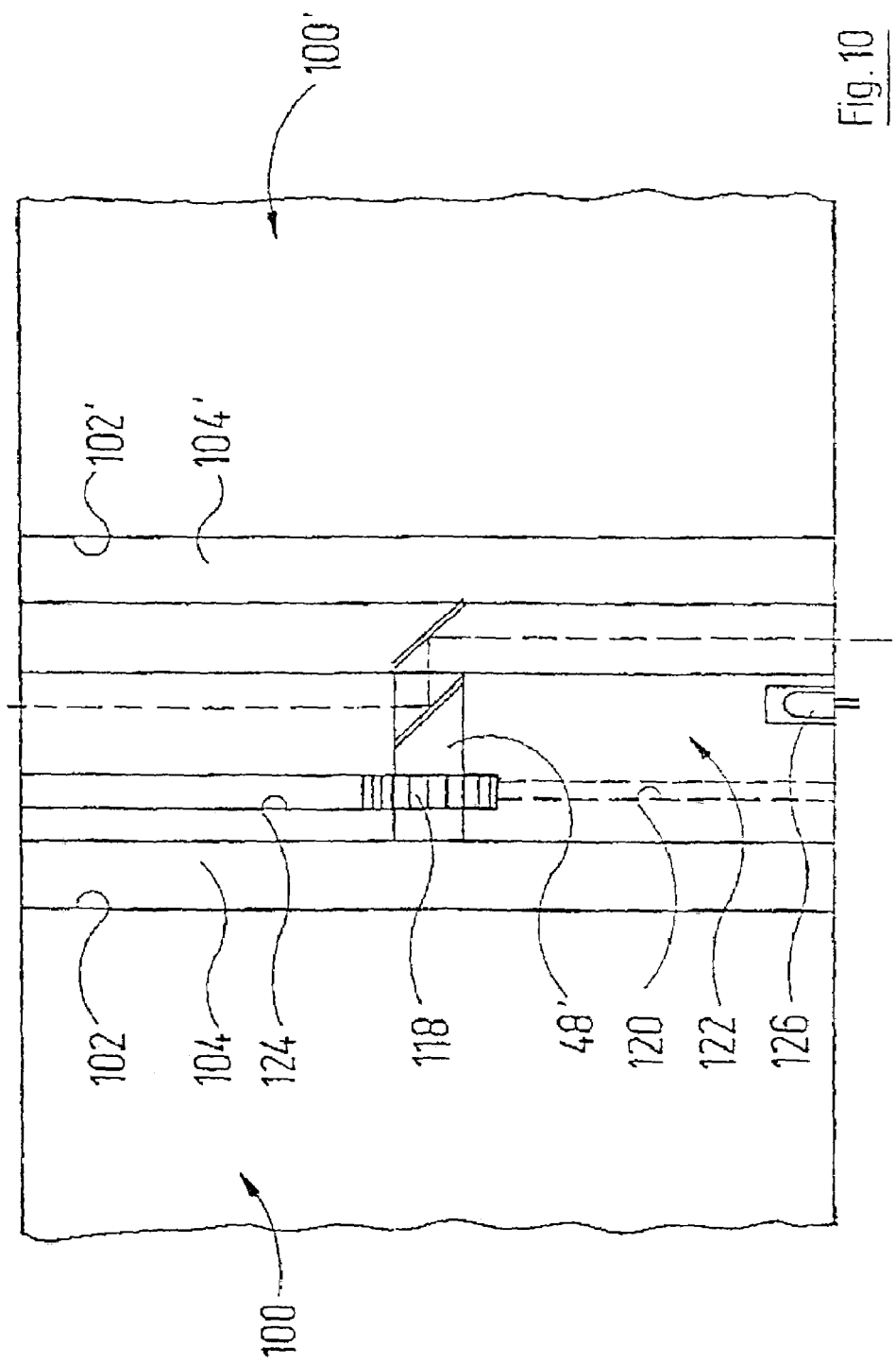
FIG. 10 is a schematic axial section through a modified scanning unit for use in a scanner for reading out storage foils.

In the scanner of FIG. 10 the end wall 30 is replaced by the entrance window 102' of a further photomulitplier 100', opposing the photomulitplier 100 such that the overall arrangement is symmetric with respect to the plane of slot 82. The output signals of the two photomultipliers 100 and 100' are electrically added and are then further processed as has been described above in connection with photomulitplier 100.

A further modification of the scanner shown in FIG. 10 resides in the fact that the prism carrying member 48 has a turbine rotor 118 formed integral therewith. The turbine rotor 118 is exposed to an air jet discharged from the end of a pressure air passage way 120 formed in a transparent disk 122 overlying the color filter 104 of the photomulitplier 100. An exhaust air passage way 124 is also formed in the disk 122. The exhaust air passage way 124 vents detended air discharged from the turbine rotor 118 to the atmosphere.

For measuring the position of the pentaprism 54 (shown in FIG. 10 in a simplified way as a mirror) a photo-diode 126 is provided being arranged in an angular region which is not covered by the storage foil 12. Upon each passage of the reading out light beam 36 the diode 126 provides a triggering signal for the control unit of the scanner. The actual momentary position of the reading out light beam 36 between two successive triggering signals is being interpolated from succeeding trigger pulses on a time basis.

Figure 11:
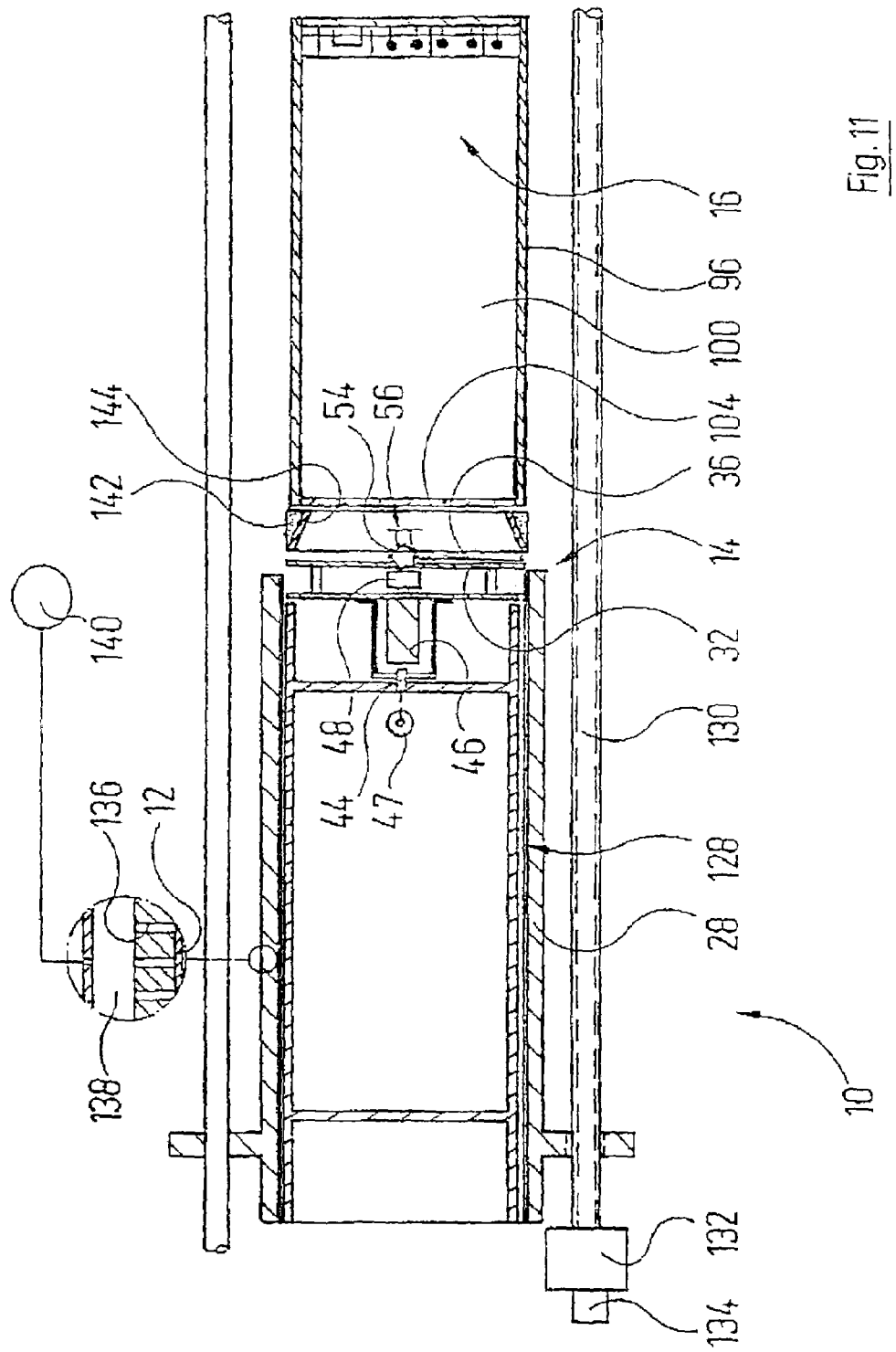
FIG. 11 is an axial section through a still further modified scanner for reading out storage foils.

In the embodiment shown in FIG. 11 components which are comparable to components already described above again carry the same reference numerals. These components are not described again in more detail. The storage foil 12 is arranged on the interior surface of a cylindrical support drum 128. The latter is movable in axial direction by means of a threaded spindle 130 driven by a drive motor 132. A position encoder 134 is associated to the drive motor 132.

Good contact of the storage foil 12 to the inward surface of the foil support 128 may be improved by perforating the peripheral wall of the foil support 128 as shown at 136. Behind the various openings 136 of this perforation there is an annular suction chamber 138 communicating with a vacuum source 140.

Deflection of the reading out light beam 36 is achieved in a way similar as described with reference to FIGS. 1 to 7. When the drive motors 46 and 132 are simultaneously energized, the light sensitive surface of the storage foil will again be scanned along a helical line of very small pitch and the output signal of the photomulitplier 100 will be recorded together with the signals output from the position encoders 47 and 134.

One recognizes that in the scanner of FIG. 11 reading of the storage foil can be achieved along the entire circumference of the foil support 128, while in the embodiment of the preceding figures reading out of the storage foil is carried out over an angle of 180°.

Furthermore in the embodiment of FIG. 11 an annular mirror 142 is arranged on that end of the support wall 96 receiving the photomulitplier, which is adjacent to the slot 82. The annular mirror 142 is formed with a frusto-conical reflecting layer 144. This is advantageous in view of capturing also fluorescence light which propagates in a direction being essentially perpendicular to the axis of the device.

In the above description of various scanners it has been supposed that these scanners are used for scanning large size storage foils, I. e. storage foils as they are used for taking panoramic images of the jaws or medical surview foils having a size of say 20×30 cm.

The scanners described above can also be used in connection with small storage foils having a size corresponding to the size of classic X-ray films used for taking intraoral images, i.e. say 3×4 cm.

In order to facilitate aligned positioning of such small storage foils the supporting wall 28 is formed with three positioning recesses 146 being aligned in axial direction with an associated one of the transport belts 70. The positioning recesses 146 are provided immediately adjacent to the plane in which the reading light beam rotates. Each positioning recess has an inclined bottom wall 148 ascending torwards the plane of rotation of the reading light beam 36. The peripheral contour of each of the positioning recesses 146 corresponds to a rectangle.

The actuating member of a micro-switch 150 projects through a small opening of the bottom walls 148, respectively. The micro switches 150 output a signal indicating that a small storage foil has been placed in the corresponding positioning recess. This output signal is used for switching the electronics of the scanner between different modes of operation as will be described below in more detail referring to FIG. 13.

In order to seal the reading gap of the scanning unit against ambient light, semi-circular brush elements 152, 154 are arranged at the upstream and downstream end of the shielding wall 83, respectively. As may be seen from the enlargement of FIG. 1, the brush elements 152, 154 comprise bristles 156, which are inclined in forward feed direction so that the storage foils can be moved past the brush elements under small friction.

Alternatively or in addition bristles may be provided which are carried by the support wall 28 and extend in radial outward direction being also inclined in forward feed direction.

While three transport belts 70 and three positioning recesses 146 are shown in the drawings in practical embodiments more or less than three such components may be provided. In a preferred practical embodiment four transport belts 70 and four aligned positioning recesses 146 are provided.

Synchronizing of the transport belts 70 can be achieved by mechanical positive coupling and/or electronic coupling. Electronic coupling means e.g. that the transport belts are driven by stepping motors which are driven by pulses received from a common control circuit. In a particularly preferred embodiment one such stepping motor may be provided to drive two transport belts by means of suitable gear units.

In the scanning unit shown in FIG. 12 components, functional equivalents of which have already been described in connection with FIGS. 1 to 12 have been given the same numerals. These components will not be described in detail again.

Figure 7:
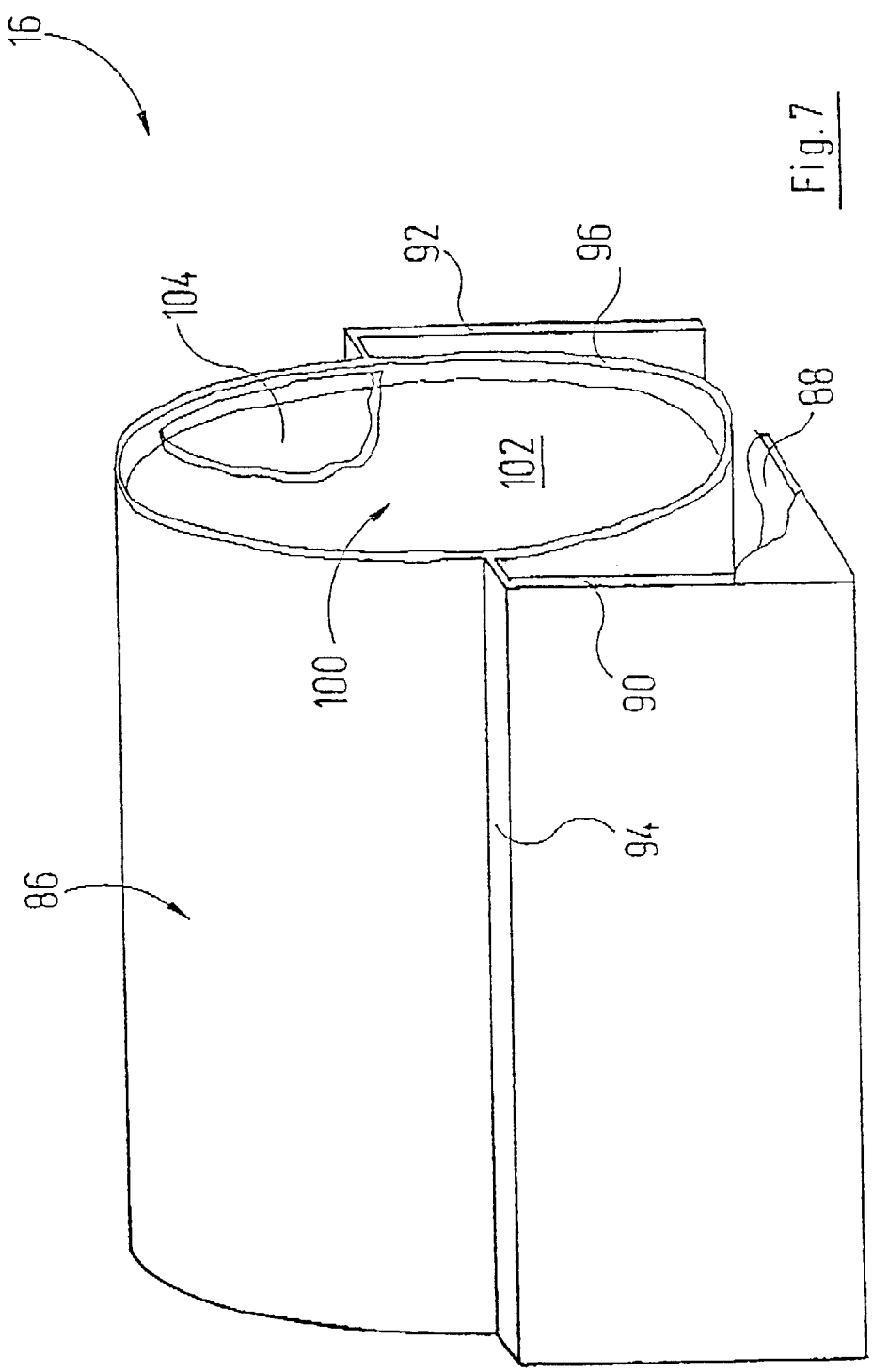
FIG. 7 is a perspective view of a detector unit of the scanner of FIG. 1.
Figure 12:
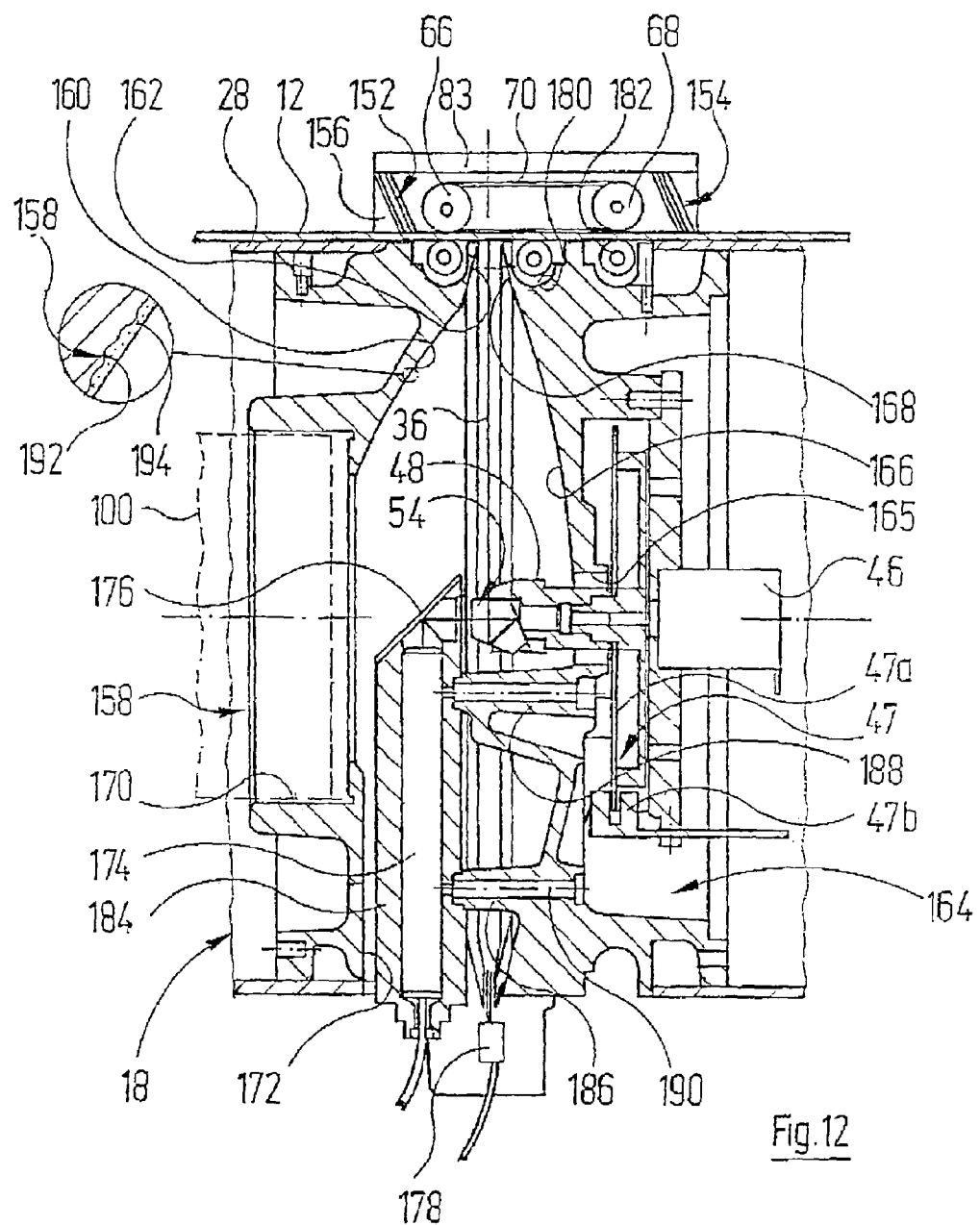
FIG. 12 is an axial section through the scanning section of a still further modified scanning unit.

The photomulitplier 100 used in the embodiment of FIG. 12 is of smaller diameter than the photomultiplier shown in FIG. 7, i.e, smaller than the diameter of the cylinder defined by the support wall 28. An annular mirror 158 receives the window end portion of the photomulitplier 100. The mirror face of the mirror 158 has an radially outward curved portion 160 and a radially inward curved mirror portion 162. Both mirror portions are of revolution, the mirror portion 160 being of large radius of curvature, while the mirror portion 162 has a smaller radius of curvature. Both mirror portions are part paraboloids of revolution.

The intermediate wall 32 has been replaced by a mirror 164 having two mirror portions 166, 168 of larger and smaller radius of curvature, respectively. The mirror 164 has a central opening 165 to receive a micromotor or a motor shaft driving the light deflecting element 56. Mirror portions 166, 168 again part paraboloids of revolution.

The mirror portion 160 has smaller radius of curvature than the mirror portion 166.

The rotary encoder 47 associated to the motor 46 is shown to comprise a slit disk 47a and a light barrier 47b. This sensor, in the embodiment of FIG. 12, is used for speed control of the motor 46, only, but not for detecting the rotary position of the reading light beam 36.

Mirror 158 is provided with a flange portion 170 receiving the window end portion of the photomulitplier 100.

In the lower portion of the annular mirror 158 a radial passageway 172 is provided which receives a short "circu" (circular beam) semi-conductor laser 174. The reading light beam provided by the latter in radial direction is deflected by a mirror 176 into the axis of the scanner. It will be rotated in the beam plane lying between the two mirrors 158 and 164 as described above.

The laser 174 is arranged in a housing 184 connected to axial studs 186, 188 of the mirror 164 by screws 190.

In the lower portion of the interspace between the two mirrors 158 and 164 there is provided a triggering photo diode 178 which will be hit by the reading light beam 36 once upon each revolution of the light deflecting element 56. This photo diode is used for measuring the actual rotary position of the pentaprism 54 and the light beam 36 as will be explained in more detail below referring to FIG. 13.

The bodies of the mirrors 158 and 164 are provided with recesses 180 receiving pressure rollers 182 supporting the storage foils in radial inward direction when being moved by the transport belts 70. Thus a good frictional contact between the transport belts 70 and the outer surface of the storage foils is warranted.

As may be seen from an enlargement of FIG. 12 the surface 192 of mirror 158 is roughened so that a diffuse reflection of light is obtained. The surface 192 carries a coating 194 which is transparent for fluorescence light and absorbs reading light. The coating 194 may be chosen so as to have diffuse reflective properties for PSL light.

The surface of mirror 164 carries a similar coating. The surface of mirror 164 may be perfectly reflecting or it may be roughened similar to surface 192 to provide for diffuse reflection of PSL light.

Figure 13:
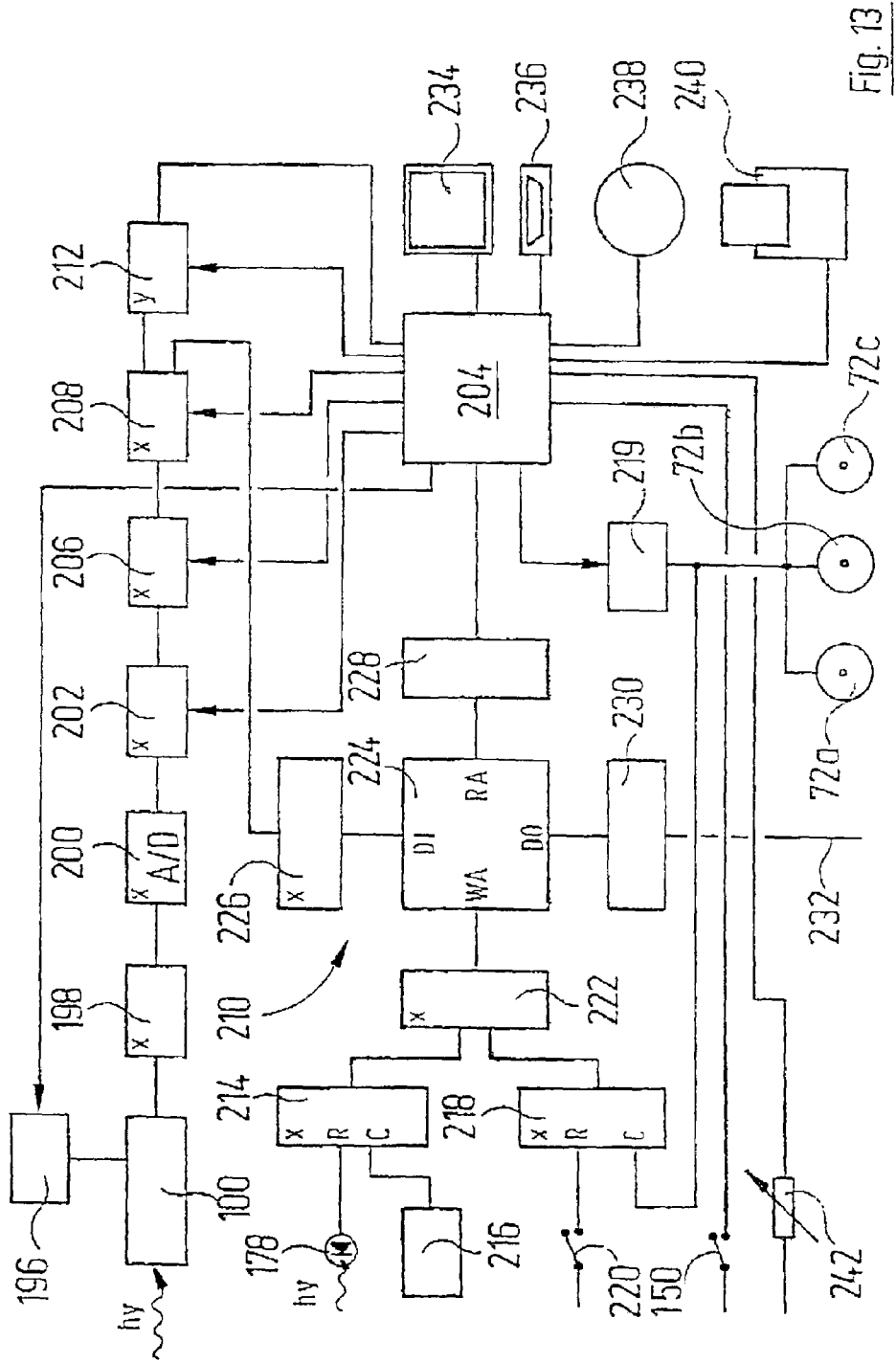
FIG. 13 is a block diagram of electronic circuitry for pre-processing and buffering signals output from a light detector of a scanner as shown in FIGS. 1 to 12.

FIG. 13 is a schematic block diagram of the electronic circuitry associated to the scanning device.

In FIG. 13 lines supplying signals which serve for controlling operation of another circuit have been marked by an arrow.

The photomulitplier 100 (and eventually an opposing further photomulitplier 100') is energized by a controllable high voltage supply 196. The photocurrent output from the photomulitplier 100 is supplied to a signal forming circuit 198 which will shape, amplify and filter the signal output from the photomulitplier in analog technique.

The signal generated by the signal forming circuit 198 is digitalized in an analog to digital convertor 200. The output signal of the latter is processed by a threshold circuit 202. The threshold circuit 202 compares the signal received from the A/D convertor 200 to a threshold signal received from a processor 204. If the signal received is smaller than the threshold value the threshold circuit will output a signal of value "0". If the received signal exceeds the threshold signal the signal will be put through to the output.

The output of the threshold circuit 202 is connected to an averaging circuit 206. The latter calculates the signal average taken over a predetermined number of succeeding image signals, the predetermined number being given by a control signal received from the processor 204. From this predetermined number of digital signals the averaging circuit 206 will output a single averaged signal. So the flux of data provided by the output of the averaging circuit 206 is only a given fraction of the incoming flux of data.

The signal output from the averaging circuit 206 is supplied to a switching circuit 208 controlled by the processor 204. The switching circuit 208 will supply those signals, which correspond to image points lying within the periphery of the storage foils arranged on the supporting wall 28 to a storing unit 210, while those signals, which correspond to regions of the scanning area which are outside the edges of the storage foils are directed to a dark current monitoring circuit 212. The latter will determine from the incoming signals an average dark current signal and an average noise signal of the dark current which signals are supplied to the processor 204.

The triggering photo diode 178 is connected to the reset terminal "R" of a counter 214. A count terminal "C" of counter 214 is connected to an output of a free running clock 216. Thus the instantaneous contents of the counter 214 is indicative of the angular position of the reading light beam 36.

A second counter 218 has a count terminal "C" receiving pulses from a free running clock 219, the operational state (ON/OFF) and working frequency of which are control-led by the processor 204. The pulses provided by the clock 219 are used to control the three stepping motors 72 associated to the three transport belts 70 so as to synchronously cooperate with corresponding portions of the storage foil being scanned.

The second counter 218 further has a reset terminal "R" receiving a signal when an end switch 220 cooperating with the axial drive unit for the storage foils is actuated. The end switch 220 may be a micro-switch or a light barrier or the like. Thus the actual contents of counter 218 is indicative of the axial position of a storage foil being scanned with respect to the beam plane (i.e. The plane in which the reading light beam 36 rotates).

The output signals of counters 214 and 218 are combined into a single addressing signal by juxtaposition or concatenation by a write address circuit 222. The latter is connected to write address terminals "WA" of a fast solid state read/write memory 224 (RAM). Data input terminals "DI" of the latter receive data from a write control circuit 226, the input of which is connected to the first output of the switching circuit 208.

A read address circuit 228 is controlled by the processor 204. Its output is connected to read address terminals "RA" of the memory 224.

Data output terminals "DO" of the memory 224 are connected to a read control circuit 230, the output of which is connected to a data line 232 which may be connected to an external computer used for further processing of the image data like enhancement of contrast, scaling, rotation of the image and the like.

The components 222 to 230 together form the storing unit 210.

The circuits 198 to 226 are clocked in accordance with clock signals of appropriate frequency, which are provided by the clock 216, which in addition to the output connected to counter 214 has further outputs of higher frequency not shown in detail. The circuits clocked by the clock 216 have been marked by a small cross in the upper left corner of the respective box. One recognizes that the image signal acquisition and storing of the image signals is at high speed in real time, while reading out image signals from the memory 224 may be achieved at a lower rate in accordance with the data transfer capacity of data line 232.

The processor 204 is connected to a monitor 234 and a keyboard 236 for controlling working of the scanning device and giving messages to a user. The processor 204 cooperates with a mass storage like a hard disk 238 and may be connected to a printer 240 for outputting images, if desired.

The processor 204 operates in accordance with programs stored on the hard disk 238 or in a ROM. Changes of its operation may be effected by entering commands and data via keyboard 236. Further means to modify the working of processor 204 are the micro-switch 150, the output signal of which informs the processor 204 on the kind of storage foils to be scanned. Normally the small storage foils for taking dental intraoral images are not only of different dimension but also of different sensitivity as compared to the large storage foils used for panoramic images. So in accordance with the signal output from the micro-switch 150 the processor 204 may not only know the edges of the storage foil and program the switching circuit 208 correspondingly, but the processor 204 may also program the high voltage output from the high voltage supply 196 in accordance with the sensitivity of the storage foil used such that the overall range of output signals received from the photomulitplier 100 essentially corresponds to the overall working range of the A/D converter 200.

A further input terminal of the processor 204 is connected to a manually adjustable signal source which has been presented by an adjustable resistor 242. This resistor may be used to define part of the control signal supplied to the high voltage supply 196 by the processor 204. By doing so the scanner is adjusted to local scanning conditions including stray light, type of storage foils used, type of photomulitplier used, optical densities preferred by the respective user and so on.

A further output terminal of the processor 204 controls the free running clock 219, the output signal of which is used for activating stepping motors 72-1, 72-2 and 72-3 associated to the three transport belts 70. Thus electronic synchronization of the three transport belts is achieved and the pitch of the helical scanning line or the distance between successive scan lines is determined. The signal output from clock 219 is also supplied to the count terminal "C" of counter 218 as has been pointed out above.

Figure 14:
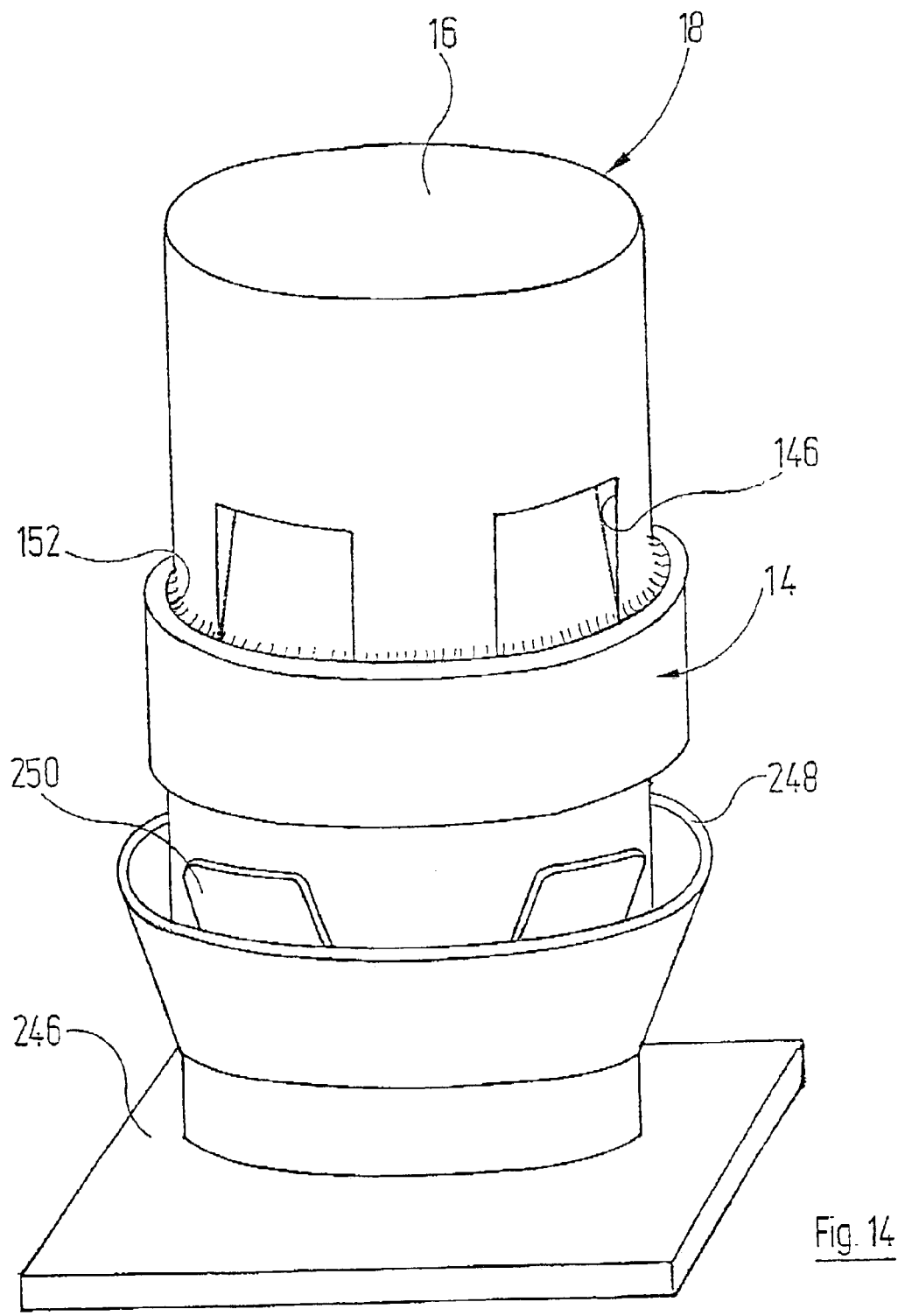
FIG. 14 is a side elevational view of a still further scanner.

FIG. 14 shows a modified scanning device, which as to function is comparable to the one explained above referring to FIGS. 1 to 7. Components being functionally equivalent to components already shown in this figures are given the same reference numerals, even if they differ in geometry.

The main differences between the embodiment of FIG. 14 and the embodiment of FIGS. 1 to 7 resides in the fact that the supporting wall 28 and the main housing body 18 are of revolution and that the axis of the scanner if vertical. The main housing body 18 is carried by a horizontal base plate 246.

A storage foil capturing wall 248 of frusto-conical geometry is provided under the scanning and transport unit 14. Thus storage foils 250 for taking small dental intraoral images are captured after leaving the scanning and transport unit 14. The axial dimension of the capturing wall is smaller than the length of the storage foils 250 so that the upper end of the discharged storage foils 250 can be easily grasped.

In a further embodiment not shown in the drawings the belt drives feeding the storage foil in axial direction may be replaced by friction wheels or friction rollers (or groups of such wheels or rollers arranged along generating lines of the cylinder surface defined by the support wall 28) which are mechanically or electrically coupled for synchronous operation.

In the above description reference has been made to the storage foils as such. It is to be understood, that these storage foils are actually used together with foil holders or light tight one way envelopes. These components are removed before scanning of the latent images of the storage foils and are applied to the storage foils after reconditioning for further use (erasure of remnant storage centers).

The foregoing description merely explains and illustrates the invention and the invention is not limited thereto except insofar as the appended claims are so limited, as those having skill in the art who have the disclosure before them will be able to make modifications without departing from the scope of the invention.

What is claimed is:

1. A light detector unit for use in an information reading device for reading flexible information carriers which are bent into at least partly cylindrical geometry by positioning on an information carrier support that is at least partially cylindrical, comprising a light detector arranged on an axis of the information carrier support, the light detector having an entrance window and a radius that essentially corresponds to a radius of the at least partially cylindrical surface of the information carrier support.

2. The detector unit as in claim 1, wherein a second light detector is provided which is arranged symmetric to the light detector with respect to a plane perpendicular to the axis of the information carrier support.

3. A light detector unit for use in an information reading device for reading flexible information carriers which are bent into at least partly cylindrical geometry by positioning on an information carrier support that is at least partially cylindrical, comprising a light detector arranged on an axis of the information carrier support, the light detector having an entrance window, wherein the light detector has a radius smaller than a radius of the at least partially cylindrical surface of the information carrier support and an entrance end of the light detector is received in an annular mirror, the annular mirror having an outer radius that essentially corresponds to the radius of the at least partially cylindrical surface of the information carrier support.

4. The detector unit as in claim 3, characterized in that a second mirror is provided which opposes the light detector with respect to a plane that is perpendicular to an axis of the information carrier support.

5. The detector unit as in claim 4, wherein the second mirror is formed with a hole receiving a motor shaft or a housing of a miniature motor.

6. The detector unit as in claim 3, characterized in that the annular mirror has a frustoellipsoid or frustoparabolic reflecting surface.

7. The detector unit as in claim 4, characterized in that the second mirror has a frustoellipsoid or frustoparabolic reflecting surface.

8. The detector unit as in claim 3, characterized in that the annular mirror comprises mirror layers which are provided on a circumferential surface of the annular mirror and a back surface of a color filter, wherein the color filter is transparent to fluorescence light received from an information carrier formed by a storage foil, and the color filter absorbing reading light directed to the information carrier for exciting metastable storage centers of the storage foil into fluorescent centers.

9. The detector unit as in claim 4, characterized in that the second mirror comprises mirror layers which are provided on a circumferential surface and a back surface of a color filter, wherein the color filter is transparent to fluorescence light received from an information carrier formed by a storage foil, and the color filter absorbing reading light directed to the information carrier for exciting metastable storage centers of the storage file into fluorescent centers.

10. The detector unit as in claim 4, wherein the second mirror has a mirror surface formed by two merging surfaces of revolution, the surfaces of revolution including a radially outer surface that has a large radius of curvature, and a radially inward surface that has a smaller radius of curvature.

11. The detector unit as in claim 3, characterized in that the annular mirror has a mirror surface that is roughened to provide for diffuse reflection of light.

12. The detector unit as in claim 4, characterized in that the second mirror has a mirror surface that is roughened to provide for diffuse reflection of light.

13. The detector unit as in claim 3, characterized in that the annular mirror is a cast component.

14. The detector unit as in claim 13, wherein the annular mirror is a cast aluminum or aluminum alloy component.

15. The detector unit as in claim 4, characterized in that the second mirror is a cast component.

16. The detector unit as in claim 15, wherein the second mirror is a cast aluminum or aluminum alloy component.

17. The detector unit as in claim 3, characterized in that the annular mirror has a mirror surface coated with a layer that is transparent to light received from the information carrier and capable of absorbing reading light directed to the information carrier.

18. The detector unit as in claim 4, characterized in that the second mirror has a mirror surface coated with a layer that is transparent to light received from the information carrier and capable of absorbing reading light directed to the information carrier.

19. The detector unit as in claim 5, wherein the motor shaft or the shaft of the miniature motor carries a light deflecting element capable of receiving a reading light beam in an axial direction and then providing a rotating reading light beam in a plane perpendicular to the axis of the information carrier support.

20. The detector unit as in claim 19, wherein the information carrier support is provided with a circumferential slot exposing a radially inward facing circumferential portion of an inner surface of the information carrier arranged on the information carrier support to the rotating reading light beam.

21. The detector unit as in claim 19, wherein the light deflecting element comprises a pentaprism.

22. The detector unit as in claim 19, wherein the reading light beam is directed to the axis of the information support carrier by a deflecting mirror arranged on the axis of the information support barrier.

23. The detector unit as in claim 22, wherein the reading light beam is directed onto the deflecting mirror by means of a second deflecting mirror arranged under radial distance from the axis of the information carrier support.

24. The detector unit as in claim 23, wherein the deflecting mirror arranged on the axis of the information support carrier and the second deflecting mirror arranged under radial distance from the axis of the information carrier support are formed on opposing inclined end faces of a one-piece optical wave guide.

* * * * *